US008148087B2

(12) United States Patent
Laskey et al.

(10) Patent No.: US 8,148,087 B2
(45) Date of Patent: Apr. 3, 2012

(54) DETECTION OF DYSPLASTIC OR NEOPLASTIC CELLS USING ANTI-MCM6 ANTIBODIES

(75) Inventors: Ronald A. Laskey, Cambridge (GB); Gareth H. Williams, Cambridge (GB); Nicholas Coleman, Cambridge (GB)

(73) Assignee: Cancer Research Technology Limited, London (GB)

( * ) Notice: Subject to any disclaimer, the term of this patent is extended or adjusted under 35 U.S.C. 154(b) by 329 days.

(21) Appl. No.: 12/264,456

(22) Filed: Nov. 4, 2008

(65) Prior Publication Data

US 2010/0143943 A1    Jun. 10, 2010

Related U.S. Application Data

(62) Division of application No. 11/365,659, filed on Mar. 2, 2006, now Pat. No. 7,459,157, which is a division of application No. 09/922,652, filed on Aug. 7, 2001, now Pat. No. 7,056,690, which is a division of application No. 09/175,947, filed on Oct. 21, 1998, now Pat. No. 6,303,323.

(60) Provisional application No. 60/071,245, filed on Dec. 22, 1997, provisional application No. 60/086,885, filed on May 27, 1998, provisional application No. 60/095,966, filed on Aug. 10, 1998.

(30) Foreign Application Priority Data

| Oct. 21, 1997 | (GB) | 9722217.8 |
|---|---|---|
| Nov. 14, 1997 | (GB) | 9724134.3 |
| Feb. 26, 1998 | (GB) | 9804156.9 |
| May 15, 1998 | (GB) | 9810560.4 |
| Aug. 5, 1998 | (GB) | 9817075.6 |

(51) Int. Cl.
*C12Q 1/68* (2006.01)

(52) U.S. Cl. ................ 435/7.1; 424/130.1
(58) Field of Classification Search .................. None
See application file for complete search history.

(56) References Cited

U.S. PATENT DOCUMENTS

| 5,851,821 A | 12/1998 | Williams et al. |
| 6,007,996 A | 12/1999 | McNamara et al. |
| 6,303,323 B1 | 10/2001 | Laskey |
| 7,056,690 B2 | 6/2006 | Laskey |
| 7,459,157 B2 | 12/2008 | Laskey et al. |
| 2007/0275421 A1 | 11/2007 | Laskey et al. |

FOREIGN PATENT DOCUMENTS

| EP | 0 157 613 A2 | 10/1985 |
| EP | 0 812 594 A1 | 12/1997 |
| WO | WO 9716731 A1 | 5/1997 |
| WO | 97/41153 | 11/1997 |
| WO | 98/09170 | 3/1998 |

OTHER PUBLICATIONS

Tockman et al (Cancer Res., May 1992, 52(9Suppl):2711s-2718s).*
Chatrath et al, "Aberrant expression of minichromosome maintenance protein-2 and Ki67 in laryngeal squamous epithelial lesions", British Journal of Cancer (2003), vol. 89, pp. 1048-1054.
Scott et al, "A novel immunohistochemical method to estimate cell-cycle phase distribution in archival tissue: implications for the prediction of outcome in colorectal cancer", Journal of Pathology, 2003, vol. 201, pp. 187-197.
Davies et al, "Increased expression of minichromosome maintenance protein 2 in active inflammatory bowel disease", Colorectal Disease, 2004, vol. 6, pp. 103-110.
Dudderidge et al, "Mcm2, Geminin, and K167 Define Proliferative State and Are Prognostic Markers in Renal Cell Carcinoma", Clin Cancer Res 2005, vol. 11, No. 7, pp. 2510-2517.
Wharton et al, "Replicative Mcm2 protein as a novel proliferation marker in oligodendrogliomas and its relationship to Ki67 labelling index, histological grade and prognosis", Neuropathology and Applied Neurobiology, 2001, vol. 27, pp. 305-313.
Hiraiwa, et al., "Specific distribution patterns of hCDC47 expression in cutaneous diseases", Journal of Cutaneous Pathology Jul. 1998; 25(6): 285-290.
Immunolocalization of Hcdc47 Protein in Normal and Neoplastic Human Tissues and Its Relation to Growth, Int J. Cancer (Pred. Oncol.): 74, 180-184(1997) 1997.
Williams et al., "A human protein related to yeast Cdc6p", Abstract, Proc. Natl. Acad. Sci. USA (1997), 94 (1), 142-147.
Hiraiwa et al., "Immunolocalization of hCDC47 protein in normal and neoplastic human tissues and its relation to growth", Abstract, Int. J. Cancer (1997) 74 (2), 180-184.
Williams et al., "Improved cervical smear assessment using antibodies against proteins that regulate DNA replication", Abstract, Proc. Natl. Acad. Sci. USA (Dec. 8, 1998) 95 (25) 14932-7.
Hiraiwa et al., "Immunolocalization of hCDC47 Protein in Normal and Neoplastic Human Tissues and Its Relation to Growth", Int. J. Cancer 74, 180-184 (1997)—The Article.
Todorov et al "HsMCM2/BM28: A Novel Proliferation Marker for Human Tumors and Normal Tissues", Laboratory Investigation, Jan. 1998, vol. 78, No. 1, pp. 73-78.
Gavin et al, Science 1995; vol. 270, pp. 1667-1671.

(Continued)

*Primary Examiner* — Laura B Goddard
*Assistant Examiner* — Meera Natarajan
(74) *Attorney, Agent, or Firm* — Nixon & Vanderhye P.C.

(57) ABSTRACT

Determination of cellular growth abnormality, particularly cancerous abnormality, by detection of target polypeptides or encoding mRNA, where the target polypeptides are members of the preinitiation complex of DNA replication in tissue, cells or fluid. Target polypeptides include CDC6, MCM2, MCM3, MCM4, MCM5, MCM6 and MCM7. Test samples include tissue of the cervix (both biopsy and smear samples), breast, colon, lung, bladder, skin, larynx, oesophagus, bronchus, lymph nodes and urinary tract (both biopsy and cytology smear samples), in determination of cancerous and precancerous cellular growth abnormality, and cells spun from urine, blood and serum, in determination of haematological malignancies and evidence of metastatic sarcoma and carcinoma.

4 Claims, No Drawings

OTHER PUBLICATIONS

Todorov et al, "A human nuclear protein with sequence homology to a family of early S phase proteins is required for entry into S phase and for cell division" J. Cell Science 1994, 107, 253-265, GenBank Acc. No. X67334.

Werness et al, "Expression of the proliferation antigen BM28/hMCM2 in human tumors and normal tissue", Laboratory Investigation, vol. 76, No. 1, p. 185A, Mar. 1997.

Murphy et al, Clinical Oncology, American Cancer Society, $2^{nd}$ edition, 1995, pp. 553-554.

* cited by examiner

SEQUENCE LISTING

```
<160> NUMBER OF SEQ ID NOS: 1

<210> SEQ ID NO 1
<211> LENGTH: 17
<212> TYPE: PRT
<213> ORGANISM: Artificial Sequence
<220> FEATURE:
<223> OTHER INFORMATION: Description of Artificial Sequence: CONSENSUS
      SEQUENCE COMMON TO MCM FAMILY OF PEPTIDES

<400> SEQUENCE: 1

Val Val Cys Ile Asp Glu Phe Asp Lys Met Ser Asp Met Arg Thr Ala
 1               5                  10                  15

Cys
```

DETECTION OF DYSPLASTIC OR NEOPLASTIC CELLS USING ANTI-MCM6 ANTIBODIES

The present application is a divisional of application Ser. No. 11/365,659, filed Mar. 2, 2006 (allowed, which published as US 2007/0275421 A1 on Nov. 29, 2007), which is a divisional of application Ser. No. 09/922,652, filed Aug. 7, 2001 (issued as U.S. Pat. No. 7,056,690), which is a divisional of Ser. No. 09/175,947, filed Oct. 21, 1998 (issued as U.S. Pat. No. 6,303,323) and claims benefit of U.S. Provisional Application Nos. 60/071,245, filed Dec. 22, 1997, 60/086,885, filed May 27, 1998 and 60/095,966, filed Aug. 10, 1998 and UK 9722217.8, filed Oct. 21, 1997, UK 9724134.3, filed Nov. 14, 1997, UK 9804156.9, filed Feb. 26, 1998, UK 9810560.4, filed May 15, 1998 and UK 98170756, filed Aug. 5, 1998, the entire content of each of which is hereby incorporated by reference in this application.

The present invention relates to assessment of cells in a sample of tissue, cells or fluid with a view to detecting cellular growth abnormality, particularly potentially (or actually) cancerous cells. Aspects of the present invention are particularly useful in screening samples such as cervical smears from women to detect those whose cervical cells are abnormal. The invention is also applicable to assessment of cells in other tissue samples, including breast, as demonstrated experimentally herein. Samples found to be abnormal may be examined in more detail and the condition of cells in the tissue investigated further. Identification of a malignant or pre-malignant condition may be followed by appropriate treatment following more extensive diagnostic procedures.

The present invention is based on the surprising discovery that specific binding molecules directed against particular proteins of the preinitiation complex of DNA replication can be used to detect abnormal cells. Especially useful in the present invention are binding molecules directed against Cdc6. Also especially useful are binding molecules directed against MCM proteins, particularly MCM5. Experimental evidence included herein shows that specific binding molecules directed against Cdc6, and also those against MCM2, MCM3, MCM4, MCM5, MCM6 or MCM7 are much more effective in marking cellular growth abnormality in tissue samples than antibodies against PCNA and Ki67. A priori one would have expected Cdc6 and the MCM's to give similar results as Ki67 and PCNA, since all these proteins can be considered "proliferation markers". On cervical samples subject to antigen retrieval (pressure cooking or autoclaving), experimental results below show that in fact results obtained are similar for all these, but there is clear difference on cervical smears and frozen samples. Such samples, of primary interest for screening purposes, are not robust enough to be subject to pressure cooking. Of particular interest in the context of screening are the very strong and clear results obtained with assessment of cervical samples using anti-Cdc6 or anti-MCM binding molecules, showing high-level staining of abnormal cells, and full-thickness staining in LSIL samples. This indicates usefulness in assessment of smear samples taken from the cervical epithelial surface—and indeed this is verified experimentally herein. Full thickness staining is also seen for HSIL samples.

Experimental assessment of abnormality in breast tissue, urine, blood and serum confirms generality of aspects of the present invention. Further evidence is provided by the use of the same antibodies in detection of the presence of dysplastic or neoplastic cells in body fluids by biochemical methods that can be automated. Examples demonstrated herein include detection of bladder cancer by analysis of urine and detection of both leukemia and lymphoma by analysis of blood. A suitable method for such analysis is Dissociation Enhanced Lanthanide Fluorescence Immunoassay, "DELFIA". Also included is demonstration of detection of sarcoma and carcinoma cases by DELFIA on blood.

The cervical epithelium is essentially composed of two distinct cell types: the squamous epithelium and the columnar epithelium, each of which is located in an anatomically distinct region of the tissue. The squamous epithelium is located at the exterior aspect (the ectocervix) of the cervical opening (os), while the columnar epithelium extends into the endocervical canal (the endocervix). These two distinct epithelial cell types come into contact in the vicinity of the cervical os, at the squamo-columnar junction. The squamo-columnar junction is of clinical importance as it is the region where the majority of malignancies arise. For diagnostic validity, a cervical smear sample should include cells from this region. In order to ensure that this has been achieved, a smear should contain columnar as well as squamous epithelial cells.

Most cervical tumours arise at the squamo-columnar junction from the squamous epithelium, which is a multilayered dynamic stem cell system under constant renewal. The stem cell compartment itself is located adjacent to the basement membrane within the basal cell layer. Stem cell division gives rise to parabasal, intermediate, and superficial cell derivatives. These are conventionally defined in terms of both their characteristic morphology and location within the squamous epithelium. The transition from basal cells located in the deepest layer of the squamous epithelium, to superficial cells at its surface is associated with progressive differentiation and a loss of proliferation until superficial squamous epithelial cells at the cervical surface are terminally differentiated.

In dysplasia, there is increased cellular proliferation with a reduction in differentiation of cells as they progress through the squamous epithelium. Typically, for convenience in the first instance, cervical screening involves assessment of smears taken from the surface of the epithelium, the cytopathologist looking for abnormalities at the surface representative of reduced differentiation as a result of dysplasia.

At the late foetal stage, during adolescence and in pregnancy columnar epithelium is replaced at the junction by squamous epithelium by a process of metaplasia. Metaplastic squamous cells which replace columnar cells are particularly vulnerable to carcinogens. Normal metaplasia should not be confused with abnormal dysplasia within the squamous epithelium, and it can be important in screening contexts to be able to distinguish between metaplastic and dysplastic cells.

Despite an intensive and expensive national screening programme, carcinoma of the cervix is the eighth most common malignancy of women in the UK and the most common malignancy in women under 35 years of age (Cancer Research Campaign, *Cancer of the cervix uteri*. 1994, CRC: London). In the developing world it is the most common malignancy and the leading cause of death in women between the ages of 35-45 years, with an estimated 437,000 new cases each year (Cancer Research Campaign, *Cancer—world perspectives*, 1995, CRC: London).

The majority of cases represent squamous cell carcinoma (SCC) and are strongly associated with infection with 'high-risk' types of human papillomavirus, such as 16, 18 and 31 (Park, et al. Cancer, 1995, 76 (10 Suppl.): p. 1902-13). Cervical carcinoma is amenable to prevention by population screening, as it evolves through well-defined non-invasive 'intraepithelial' stages (Wright, et al. *Precancerous lesions of the cervix, in Blaustein's pathology of the female genital tract*. R. J. Kurman, Editor. 1994, Springer-Verlag: New York. p. 229-78). Squamous intraepithelial abnormalities may be classified using 3 tier (CIN) or 2 tier (Bethesda) systems. Different histological abnormalities broadly correlate with the type of infecting HPV and with the DNA ploidy, clonality and natural history of the lesion. As classified by the Bethesda system, low grade squamous intra-epithelial lesions (LSIL), corresponding to CIN1 and cervical HPV infection (HPVI) generally represent productive HPV infections, with a relatively low risk of progression to invasive disease (Wright and Kurman. *A critical review of the morphological classification systems of preinvasive lesions of the cervix: the scientific basis for shifting the paradigm, in Papillomavirus reviews: current research on papillomaviruses*, C. Lacey, Editor. 1996, Leeds University Press: Leeds). High-grade squamous intra-epithelial lesions (HSIL), corresponding to CIN2 and CIN3, show a higher risk of progression than CIN1 (LSIL) though both are viewed as representing a potential precursor of malignancy. Although it is possible to estimate the approximate risk of malignancy for each category of intra-epithelial lesion, it is currently not possible to determine the approximate likelihood of progression for an individual case.

In 1943, Papanicolau and Trout introduced the Pap smear test to detect precursors of cervical cancer in women. This is a cytological screening test and has probably proved to be the most successful public health measure introduced for the prevention of cancer. Mass screening programmes, in which women have cervical smear tests at least once every three to five years, have proven highly effective in some countries in reducing cervical cancer mortality and morbidity rates. In British Columbia and Finland for example, organised screening has reduced mortality rates for cervical cancer by 70%. If detected early, cervical cancer is easily treated.

In spite of these achievements, the reality of the situation world-wide is depressing. Of the hundreds of thousands of women who develop cervical cancer annually, more than 50% will die of the disease. Seventy five percent of all those women will be in the developing world, where because of financial constraints, mass screening programmes using available methodologies are non-viable. Even in many developed countries, the decline of the disease in the past decade has been insignificant, while the impact of cytological screening has been far less than expected. In addition, experts observe a substantial proportion of cases of invasive cervical cancer in patients who are regularly screened, particularly young women.

The major reasons why cytological screening sometimes fails to detect cervical cancer are the large intervals between tests and also the high number of false negative results (10-30%) (*Pap Cytology screening: Most of the benefits reaped?* WHO and EUROGIN release a report on cervical cancer control. Press Release WHO/25, March 1997).

The high number of false negative results reflects the fact that interpretation of Pap smears is one of the most difficult of morphological exercises. The results of a Pap smear are harder to interpret than those of fine needle aspiration, body fluid cytological testing or biopsies because of the complexity and variability of the mixed cell population placed on the smear and the wide range of inflammatory and reparative processes that occur in the cervix. There are also cyclical changes in the cellular population, pregnancy induced alterations and alterations that occur in the postmenopausal period. Because gynaecological cytology is so difficult, the training periods for cytotechnologists are long; they require an educated student and high degree of discipline and pattern recognition skills. Even after completing an adequate training programme, cytotechnologists require several years of practical experience before they can make consistently accurate judgements as to whether a Pap smear result is normal or abnormal. Similarly, although pathologists may be trained to interpret histological sections, they require specialised additional training in cytopathology to possess adequate skills to organise and supervise the cytology laboratory and to make appropriate diagnoses concerning abnormal smears.

The two major problems associated with Pap screening programmes are an apparently unavoidable false negative rate (10-30%) and the relatively high cost of screening. Therefore, alternative approaches are now being considered to cervical screening. The two most commonly discussed proposals are to use HPV DNA testing and typing as a primary screening modality or as a supplement to Pap smears and to use instruments that can automatically screen conventionally taken Pap smears, thus reducing the need for the relatively highly paid cytotechnologists and cytopathologists (Richart, Cancer Supplement, 1995, 76(10): 1919-1927; Birdsong, Human Pathology, 1996, 27(5): 468-481).

The former method remains problematical. There are problems of sensitivity and positive predictive value using in-situ methods for HPV. The use of PCR for HPV DNA detection produced such high rates of HPV infection in the general population that HPV DNA testing is thought to be of questionable use for clinical screening.

The second approach involves automation. A number of companies are currently developing and marketing automated screening instruments. In general such instruments use a high resolution video scanner to capture images, which are then digitalised and analysed with a series of algorithms, and the data are then passed through an interference network through which the machine has been trained to distinguish between normal and abnormal cellular components. It is hoped that with further software and hardware development, automated screening can be considered for primary screening, though at the moment no devices have been approved for the pre-screening or independent screening of Pap smears by the US FDA. That companies are prepared to invest so heavily in such an expensive and complex approach in attempting to overcome problems with conventional PAP smear testing illustrates the severity of the problems and the heart-felt need for a solution.

Assessment of cell proliferation markers has not previously provided any such solution and experts in the field have been sceptical that proliferation markers will provide useful clinical information (Hall and Coates, Histopathology, 1995, 26: 105-112). There is a belief that measuring parameters of cell proliferation will provide objective information about tumours, but despite numerous studies there is little direct evidence that the use of cell proliferation markers such as PCNA, Ki67 etc. are really an improvement on conventional histological assessment optimally employed. Few studies have even addressed the critical issue of the relative value of proliferation markers compared to the standard histopathological grading and staging.

Attempts to use immunocytochemical or immunofluorescent staining with automated cervical screening have been limited by non-specific staining of normal cells. For example, epithelial membrane antigen (EMA) has been shown to stain neoplastic cells from cervices with CIN, but staining of some metaplastic cells from normal cervices was also reported. Therefore, although technology for measuring immunohistological staining is available, none of the automated screening machines that are on the market or in advanced development use immunohistochemistry at this time.

The most widely studied markers of proliferation are Ki67, a protein of unknown function and PCNA (proliferating cell nuclear antigen) (Yu and Filipe, Histochemical Journal, 1993, 25: 843-853). PCNA is involved in the elongation of DNA replication and in the mechanism of DNA repair. Therefore it is present during actual DNA synthesis by replication or repair.

The present inventors have studied proteins involved in the earlier initiation stage of DNA replication. These are Cdc6 and proteins of the MCM2-7 family (MCM2, MCM3, MCM4, MCM5, MCM6 and MCM7). Williams et al (1997) (Proc. Natl. Acad. Sci. USA, 1997, 94: 142-147) reported that human HeLa Cells in culture express Cdc6 throughout proliferating cell cycles, but that WI38 human diploid fibroblasts stop expressing Cdc6 when made quiescent by serum starvation. It is shown herein that these observations extend to other cell lines and other species. MCMs are present in G1 phase nuclei (before DNA synthesis) and are progressively displaced from chromatin into the soluble nucleoplasm during DNA synthesis. It is shown herein that they too are absent from chromatin during quiescence. It is also demonstrated herein that MCM5 is absent from differentiated cells of the uterine cervix and breast.

From these background facts, MCMs or Cdc6 antisera would be expected to resemble the distributions of PCNA or Ki67. Further evidence for this expectation comes from Hiraiwa et al (Int. J. Cancer, 1997, 74: 180-184) who found similar immuno-staining patterns for PCNA and MCM7 (hCDC47) in several human tissues and three types of human tumour.

Surprisingly, however, the present inventors have found dramatic differences in the potential diagnostic value of MCMs and Cdc6 as compared with PCNA and Ki67.

The inventors have tested antisera raised against human MCM protein and human Cdc6 for cervical cytology. They have studied sections of normal and diseased human uterine cervix and cervical smears. They have compared the results with those obtained using PCNA and Ki67. Cdc6 antibodies or MCM (e.g. MCM5) antibodies detect LSIL (HPVI/CIN 1) lesions in the cervix more effectively than antibodies against PCNA or Ki67. Furthermore, essentially all cells of LSIL (HPVI/CIN 1) or HSIL (CIN 2/3) lesions are stained. This is in contrast to staining by other proliferation markers such as PCNA. It indicates that specific binding molecules directed to proteins of the preinitiation complex of DNA replication, particularly Cdc6 or MCM proteins (such as MCM5 but also exemplified herein for MCM2, MCM3, MCM4, MCM6 and MCM7) have exceptional diagnostic value for early detection of atypical or neoplastic cells. On cervical samples subject to antigen retrieval (pressure cooking or autoclaving), which samples are formalin fixed and paraffin embedded, anti-Cdc6 and anti-MCM antibodies give similar patterns of staining to those obtained with PCNA, but the superior results on smears, fresh and frozen samples are clear.

Thus, the present invention generally relates in various aspects to methods and means for detecting a particular target polypeptide, or mRNA encoding a target polypeptide, in tissue, fluid or cells of an individual, usually in a sample removed from the body.

Target polypeptides of the present invention such as Cdc6 and MCM proteins, such as MCM5, may be distinguished from other cellular proliferation markers which are not useful in the present invention by being included within the preinitiation complex of DNA replication. They may be distinguished by being displaced from chromatin during quiescence and differentiation. ORC2 (Gavin at al., 1995, *Science* 270, 1667-1671) for example, which is not a target for use in the present invention, may be distinguished from proteins such as Cdc6 and MCM5 by remaining bound to chromatin in quiescent cells. Orc2 is not down-regulated in quiescent cells, though other components of the ORC complex, such as Orc1, may behave differently. Cdc6 is down-regulated rapidly during quiescence and differentiation. Cultured cells arrested in G0 for as little as 48 hours do not contain any detectable Cdc6 protein. Cdc6 is not detectable in cells arrested in vitro for longer periods of time or in differentiated cells ex vivo. Cells arrested in vitro by serum starvation or contact inhibition lose chromatin-bound MCMs (after a few days), although the total level of MCMs in the cells does not decrease appreciably, at least within 14 days. Cells which undergo differentiation in vitro (e.g HL-60 cells induced to differentiate with DMSO or TPA) down-regulate MCM3 but not Orc2 (Musahl, Aussois Meeting on DNA Replication, Aussois, France, June 1997). Differentiated cells from tissues ex vivo do not express MCM proteins such as MCM2 and MCM5. The six MCM proteins MCM2-MCM7 form a multiprotein complex, which splits into two subcomplexes: MCM3 and MCM5 diner; MCM2-4-6-7 tetramer. MCM3 and MCM5 may be displaced from chromatin during S phase more slowly than MCM2-4-6-7 (Kubota at al., 1997, *EMBO J.* 16, 3320-3331). MCMs are chromatin-bound in G1, displaced during S phase and nuclear, but not bound to chromatin in G2. Cdc6 behaves similarly in yeast, though in addition to being displaced from chromatin it is also degraded, protein levels going down dramatically at G1/S transition. Further components of the preinitiation complex of DNA replication may be included in accordance with the present invention. Examples include human homologues of yeast components, such as Cdc7 protein kinase (Chapman and Johnston, *Exp. Cell Res.*, 1989, 180 419-428 (yeast), Sao at al., 1997, *EMBO J.*, 16, 4340-4351 (human-down-regulated in quiescence)), Dbf4, the regulatory subunit of Cdc7 protein kinase (Jackson et al., 1993, *Mol. Cell. Biol.* 13 2899-2908 (yeast), Masai at al., Cold Spring Harbor Meeting on Eukaryotic DNA Replication, 3-7 Sep. 1997 (human)), Cdc14 protein phosphatase (Hogan and Koshland *PNAS USA*, 1992, 89, 3098-3102 (yeast)), Cdc45, which associates with and has a similar phenotype to MCMs (Zou at al., *Mol. Cell. Biol.*, 1997, 17, 553-563 (yeast), Takisawa at al., Cold Spring Harbor Meeting On Eukaryotic DNA Replication, 3-7 Sep. 1997 (*Xenopus*)), MCM10, which associates with and has a similar phenotype to MCMs (Merchant at al., 1997, *Mol. Cell. Biol.* 17 3261-3271). Target polypeptides of the present invention may variously be said to be any of components of the DNA pre-replicative complex, components of replication competent chromatin, involved in restricting DNA replication to once per cell cycle, components of the replication license, involved in licensing chromatin for a single round of DNA replication, and assembled at replication origins before initiation of DNA replication.

Human Cdc6 amino acid sequence is disclosed in Williams et al., 1997, *PNAS USA* 94: 142-147, GenBank Acc. No. U77949.

Human MCM2 sequence is disclosed in Todorov et al., 1994, *J. Cell Sci.*, 107, 253-265, GenBank Acc. No. X67334.

Human MCM3 sequence is disclosed in Thommes at al., 1992, *Nucl. Acid Res.*, 20, 1069-1074, GenBank Acc. No. P25205.

Human MCM4 sequence is disclosed in Ishimi at al., 1996, *J. Biol. Chem.*, 271, 24115-24122, GenBank Acc. No. X74794.

Human MCM5 sequence is disclosed in Hu at al., 1993, *Nucleic Acids Res.*, 21, 5289-5293, GenBank Acc. No. X74795.

Human MCM6 sequence is disclosed in Holthoff at al, 1996, *Genomics,* 37, 131-134, GenBank Acc. No. U46838.

Human MCM7 sequence is disclosed in Hu et al., 1993, *Nucleic Acids Res.*, 21, 5289-5293.

According to the one aspect of the present invention there is provided a method of determining the presence or absence of abnormally proliferating cells or cellular growth abnormality in a sample from an individual, the method including contacting a sample with a specific binding member directed against a target polypeptide, as discussed, and determining binding of the specific binding member to the sample.

Another aspect of the present invention provides for a method of categorising a tissue as (i) normal or (ii) potentially or actually pre-cancerous or cancerous, dysplastic or neoplastic, the method including determining binding to a sample of the tissue of a specific binding member directed against a target polypeptide, as discussed. The pattern or degree of binding may be compared with that for a known normal sample and/or a known abnormal sample.

Human Cdc6 has been cloned independently by the present inventors, as described herein, but the first publication of its cloning was by Williams et al, whose paper (*PNAS USA* 94: 142-147, 1997) provides the full amino acid sequence. As demonstrated experimentally herein, anti-Cdc6 binding molecules are very effective in marking abnormality in various tissues, especially cervical samples, preferably smears. This compares with no binding to normal cervical tissue in a smear sample.

The amino acid sequence for human MCM5 is disclosed in Hu et al., 1993, *Nucleic Acids Res.*, 21, 5289-5293, GenBank Acc. No. X74795. Experimental evidence included herein shows that binding molecules directed against it, like Cdc6, are very effective in marking abnormality in various tissues, especially cervical samples, preferably smears. Obtaining high affinity antibodies against MCM5 seems easier than for Cdc6, which may reflect higher antigenicity.

Further experimental evidence included herein shows that binding molecules directed against MCM2, against MCM3, against MCM4, against MCM6 or against MCM7 are also effective in marking abnormality in tissue samples such as cervical smears. Anti-MCM5 antibodies have been found to give a stronger staining pattern than anti-MCM2 and anti-MCM7 antibodies, both overall and in the number of cells. Anti-CDC6 antibodies have been found to give a similar staining pattern to anti-MCM5.

Thus, binding of (e.g.) an anti-Cdc6 or anti-MCM specific binding member to a sample provides for categorising the tissue from which the sample is derived as abnormal, potentially or actually pre-cancerous or cancerous, dysplastic or neoplastic. In accordance with present practice upon obtaining a positive result using the Pap test, a positively-testing individual may be investigated further, for instance by means of biopsy testing and/or repeat screening. It is quite common for pre-cancerous potential not to result in an actually cancerous state. Six-monthly screening is typically used to follow progression or regression of dysplasia to allow for appropriate and timely therapeutic intervention if required.

If a tissue is categorised as potentially or actually pre-cancerous or cancerous, on the basis of detected abnormality in a tissue sample in accordance with the present invention, appropriate diagnostic and/or clinical follow-up will be called for.

It is notable that the invention is not limited to detection of cellular growth abnormality that is necessarily pre-cancerous or cancerous. Other disorders of cellular proliferation may be detected, as is demonstrated by the experimental exemplification included below, including for psoriasis (see Example 24 below) and inflammatory bowel disease such as ulcerative colitis and Crohn's disease (Examples 33 and 34). In addition to being cellular proliferation disorders in their own right, inflammatory bowel diseases may be a precursor to a cancerous state, although not in all patients, so their detection by means of the present invention may be used to provide valuable results for closer follow-up. In inflammatory bowel disease there may be sloughing of cells of the colon and bowel, allowing for analysis to be performed on fecal samples and preparations of cells from such samples. Example 32 below describes staining of fecal smears prepared by recovering cells from feces.

The present invention may be used to pre-screen samples before further analysis. The present invention may be used for screening or analysis of samples previously tested using an available technique, such as a Pap smear test or ThinPrep 2000 test. The experiments below also show that a Pap stain analysis and an analysis in accordance with the present invention, using an appropriate antibody, can be performed on the same preparations. Thus, a cervical smear for example may be tested using both the conventional Pap smear test and a test in accordance with the present invention.

A further aspect of the present invention provides a method of marking abnormal cells within a tissue sample, the method including contacting the sample with a specific binding member directed against a target polypeptide, such as Cdc6, MCM5 or other MCM as discussed, under conditions wherein the specific binding member binds to abnormally proliferating cells and not normal cells. Whether or not the specific binding member binds to the sample may be determined in order to ascertain the presence of abnormally proliferating cells within the sample.

In a further aspect the present invention provides the use of a specific binding member directed against a target polypeptide, as discussed, for determining, assessing or diagnosing the presence or absence of abnormal cellular proliferation, cellular growth abnormality, dysplasia, neoplasia, or a potentially or actually pre-cancerous or cancerous state in a tissue or sample thereof.

A specific binding molecule may be provided in a kit, which may include instructions for use in accordance with the present invention. Such kits are provided as a further aspect of the present invention. One or more other reagents may be included, such as labelling molecules, and so on (see below). Reagents may be provided within containers which protect them from the external environment, such as a sealed vial. A kit may include one or more articles for providing the test sample itself depending on the tissue of interest, e.g. a swab for removing cells from the buccal cavity, a syringe for removing a blood sample, a spatula for taking a cervical smear, a biopsy gun and so on (such components generally being sterile). A kit may include any, any combination of or all of a blocking agent to decrease non-specific staining, a storage buffer for preserving binding molecule activity during storage, staining buffer and/or washing buffer to be used during antibody staining, a positive control, a negative control and so on. Positive and negative controls may be used to validate the activity and correct usage of reagents employed in accordance with the invention and which may be provided in a kit. Controls may include samples, such as tissue sections, cells fixed on coverslips and so on, known to be either positive or negative for the presence of the target, such as Cdc6 or MCM5. The design and use of controls is standard and well within the routine capabilities of those of ordinary skill in the art.

Samples may be removed from the body using any convenient means and technique. For cervical screening, standard smear samples may be employed. Alternatively, the ThinPrep 2000 technology (Cytec Corp, Boxborough, Mass., USA) may be used. This has been cleared by the US FDA as a replacement for the conventional method of Pap smear preparation. A sample is collected into a liquid medium instead of smearing the cells onto a glass slide. An automated processor (the ThinPrep 2000 machine) is later used to collect cells from the liquid and deposit them in a thin layer on a glass slide for analysis. A spatula or swab may be used to remove endothelium cells, e.g. from the cervix or buccal cavity. Blood and other fluid samples may be removed using a syringe or needle. Other tissue samples may be removed by biopsy or tissue section.

In preferred embodiments the sample is not subject to antigen retrieval or pressure cooking/autoclaving. Antigen retrieval has long been standard in the art and is well known to those of ordinary skill. Hiraiwa at al. refer to Shin et al. (1991) *Lab. Invest.* 64, 693-702, which provides an exemplary approach. Samples may be fresh or frozen but are generally not formalin fixed or paraffin embedded. As discussed, in a particularly preferred embodiment the sample is a cervical smear. Cervical smears are not robust enough to be subject to pressure cooking. Furthermore, antigen retrieval treatment is generally not conducive to screening where a high throughput is desirable.

Experimental exemplification of aspects of the present invention included herein demonstrates applicability to the cervix, including testing cervical smears, the breast, urinary tract malignancies (tested on both biopsy tissue samples and on urine cytology smears), colon, lung, bladder, skin, larynx, oesophagus, bronchus, lymph nodes, and haematological malignancies, also blood and serum for evidence of metastatic sarcoma and carcinoma. The present invention may additionally be employed in assessment of pre-malignant abnormalities of cervical glandular epithelial cells (glandular intra-epithelial neoplasia, GIN) or pre-malignant abnormalities in other tissues. It may be particularly appropriate for employment in cytological or biochemical assessment of other clinical specimens where detection of neoplastic cells, or their distinction from cells showing reactive changes, can be very difficult. Such specimens include sputum, bronchioalveolar lavage specimens, urine and brushings from the alimentary tract (including oesophagus, stomach and pancreas, both bile duct and pancreatic duct). The present invention may be applied in histological or biological assessment of tissue where assessment of proliferation may enable more accurate prediction of clinical outcome, and/or more rational selection of therapy. Specimens may include malignancies of glandular cells (eg. lung, breast, colon, prostate, stomach), squamous cells (eg. lung, skin, oesophagus) or other epithelial cell types (eg. bladder, ureter, kidney, ovary).

The high degree of specificity observed in the experiments described below with anti-Cdc6 antibodies and anti-MCM antibodies, including various anti-MCM2, anti-MCM3, anti-MCM4, anti-MCM5, anti-MCM6 and anti-MCM7 antibodies, tested on a range of breast cancers provides for immunocytological and biochemical approaches for diagnosis of breast cancer. Such may be applied to breast biopsies or fine needle aspiration (FNA) specimens or samplings of fluid from breast ducts, allowing for use in screening programmes.

Samples to be subjected to a contact with a binding member in accordance with various aspects of the present invention may be prepared using any available technique which allows binding of a specific binding molecule to the target polypeptide, such as Cdc6, MCM5 or other MCM as discussed, determination of nucleic acid levels, enzymatic activity and so on, in accordance with different embodiments of the present invention. Various techniques are standard in the art, e.g. (for molecules such as antibodies binding target polypeptide) as used in fixing cells for the Pap test.

The reactivities of a binding member such as an antibody on normal and test samples may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding binding molecule (e.g. antibody) and reporter molecule.

One favoured mode is by covalent linkage of each binding member with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed. Further examples are horseradish peroxidase and chemiluminescence.

The mode of determining binding is not a feature of the present invention and those skilled in the art are able to choose a suitable mode according to their preference and general knowledge.

In the experiments described below, horseradish peroxidase has been employed. Further experiments have been performed using alkaline phosphatase, with similar results being achieved (for instance with cervical smears). Alkaline phosphatase may be a more sensitive detection system than horseradish peroxidase, but the developed colour is less compatible with PAP staining.

One protocol for antibody staining of cervical smears, which has been employed in embodiments of the present invention is as follows 1. Fix fresh smear for 5 minutes in 50:50 acetone:methanol. (Note than an alternative starting point where a smear has been previously fixed with "Cytofix"—an alcoholic and wax treatment that is in standard use in the UK to treat smear samples when taken to allow safe transport to a screening centre—is to remove Cytofix by soaking in methylated spirits for 10 minutes. Should a smear have been covered with any other protective layer, any appropriate treatment may be employed to expose a sample to antibody staining.)

2. Wash in Tris-buffered saline (TBS) for 5 minutes.

3. Wash to permeabilise in 4 mM sodium deoxycholate in TBS for 15 minutes.

4. Wash in TBS plus 0.3% Triton X100 for 5 minutes.

5. Repeat step 4.

6. Wash in TBS plus 0.025% Triton X100 for 5 minutes.

7. Drain excess liquid without allowing tissue to dry out.

8. Transfer slides into a humidified chamber and place on each slide 200 microlitres of 10% goat serum reagent in TBS for a minimum of 2 hours (or overnight).

9. Drain excess liquid without allowing tissue to dry out.

10. Place 200 microlitres of primary antibody diluted in TBS containing 0.1% Triton and 1% BSA onto each slide and leave overnight at 4° C. on an orbital shaker.

11. Transfer slides into racks and wash in TBS plus 0.3% Triton X100 for 5 minutes.

12. Wash in TBS plus 0.025% Triton X100 for 5 minutes.

13. Repeat step 12.

14. Drain excess liquid without allowing tissue to dry out.

15. Transfer slides into a humidified chamber and place on each slide 200 microlitres of biotinylated goat anti-rabbit secondary antibody (Dako) at 1:500 in TBS containing 1% BSA for 1 hour.

16. While slides are in secondary antibody, make up SABC solution.

17. Transfer slides into racks and wash in TBS for 5 minutes.

18. Place slides in endogenous peroxidase blocking agent with 0.6% hydrogen peroxide for 10 minutes.

19. Wash in TBS for 5 minutes.

20. Repeat step 19 twice.

21. Transfer slides into a humidified chamber and place on each slide 200 microlitres of SABC solution for 30 minutes.

22. Transfer slides into racks and wash in TBS for 5 minutes.

23. Repeat step 22.

24. Develop in DAB solution for 10 minutes.

25. Wash in running tap water for 5 minutes.

26. Place slides in Harris' haematoxylin solution for 6 seconds.

27. Wash in running tap water for 1 minute.

28. Differentiate in 0.5% hydrochloric acid for 1-2 seconds.

29. Wash in running tap water for 5 minutes.

30. Rinse in 50% methanol for 2 minutes.

31. Rinse in 70% methanol for 2 minutes.

32. Rinse in 90% methanol for 2 minutes.

33. Rinse in 100% methanol for 2 minutes.

34. Place in Orange G working solution for 2 minutes.

35. Rinse in 100% methanol for 7 seconds and agitate gently.

36. Repeat step 35.

37. Place in EA50 solution for 2 minutes.

38. Rinse in 100% methanol for 7 seconds and agitate gently.

39. Repeat step 38.

40. Place slides in xylene to clear for 5 minutes.

41. Repeat step 40 twice.

42. Apply coverslips using DEPEX mountant.

Smears for immunofluorescence may be prepared in a similar fashion (and have been). After the secondary antibody, they are incubated in strepavidin FITC-conjugated antibody for 1 hour and counterstained for DNA with propidium iodide/RNAse A (both Sigma at 50 ng/ml), then washed and mounted in glycerol/PBS/phenylenediamine.

Preferred binding molecules for use in aspects of the present invention include antibodies, natural ligands for the target, small molecules which target one or more epitopes on the target and T-cell Receptor binding domains.

Antibodies which are specific for a target of interest, such as Cdc6, MCM5 or other MCM, may be obtained using techniques which are standard in the art. Methods of producing antibodies include immunising a mammal (e.g. mouse, rat, rabbit, horse, goat, sheep, monkey or bird such as chicken) with the protein or a fragment thereof or a cell or virus which expresses the protein or fragment. Immunisation with DNA encoding the target polypeptide is also possible. Antibodies may be obtained from immunised animals using any of a variety of techniques known in the art, and screened, preferably using binding of antibody to antigen of interest. For instance, Western blotting techniques or immunoprecipitation may be used (Armitage et al, 1992, Nature 357: 80-82).

The production of monoclonal antibodies is well established in the art. Monoclonal antibodies can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. A hybridoma producing a monoclonal antibody may be subject to genetic mutation or other changes, which may or may not alter the binding specificity of antibodies produced.

As an alternative or supplement to immunising a mammal with a peptide, an antibody specific for a target may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with the target or may be one constructed using sequences obtained from an organism which has been exposed to the antigen of interest (or a fragment thereof).

Antibodies may be modified in a number of ways. Indeed, unless context precludes otherwise, the term "antibody" should be construed as covering any specific binding substance having an antibody antigen binding domain. Thus, this covers antibody fragments, derivatives, and functional equivalents, including any polypeptide comprising an immunoglobulin binding domain, whether natural or synthetic. Chimeric molecules comprising an immunoglobulin binding domain, or equivalent, fused to another polypeptide are therefore included. Cloning and expression of chimeric antibodies are described in EP-A-0120694 and EP-A-0125023.

It has been shown that the function of binding antigens can be performed by fragments of a whole antibody. Example binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, *Science,* 242, 423-426, 1988; Huston et al, *PNAS USA,* 85, 5879-5883, 1988); (viii) bispecific single chain Fv dimers (PCT/US92/09965) and (ix) "diabodies", multivalent or multispecific fragments constructed by gene fusion (WO94/13804; P. Holliger et al Proc. Natl. Acad. Sci. USA 90 6444-6448, 1993).

Recombinant expression of polypeptides, including antibodies and antibody fragments, is well-known in the art.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli*. The preferred hosts for baculovirus expression are insect cells such as the SF9 cell line.

Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known.

Following production by expression from encoding nucleic acid an antibody or other specific binding molecule directed against a target useful in the present invention, such as Cdc6, may be recovered and may be isolated, if necessary conjugated to an appropriate label or reporter, and provided for use in determination of the presence or absence of cellular growth abnormality in a tissue sample, such as a cervical smear, in accordance with the present invention as disclosed.

Levels of Cdc6 and MCM expression in tumours are much higher than in normal tissues and these antigens may be liberated into the bloodstream (e.g. due to necrosis of tumour cells) or other body fluids, e.g. urine, or feces. A specific binding molecule may be used to detect the target in a body fluid, e.g. serum, employing any technique available to those skilled in the art, such as DELFIA, ELISA, RIA, Western blotting. Tumour progression and regression may be monitored, for instance in response to treatment or in relapse. Thus a blood or other bodily fluid sample, e.g. urine, prostatic fluid, nipple fluid, serous and ascitic effusions, cerebro spinal fluid, also feces, may be assessed in accordance with the present invention. For instance, a blood sample may be assayed for the presence of a target polypeptide such as MCM5 and CDC6 using DELFIA, ELISA, RIA e.g. as described in Williams at al. *Clin. Chem. Acta,* 1986, 155, 329-344.

Determination of binding to target in vivo may be used to identify localisation of abnormal cells in the body. Labelled binding molecules against a target in accordance with the present invention may be administered to an individual and binding within the body determined. When a radionucleotide such as Iodine-125, Indium-111, Thallium-201 or Technetium-99m is attached to an antibody, if that antibody localises preferentially in tumour rather than normal tissues, the presence of radiolabel in tumour tissue can be detected and quantitated using a gamma camera or scintigraphy. The quality of the tumour image obtained is directly correlated to the signal: noise ratio. Radiolabelling with technetium-99m is described in Pak et al (1992), Nucl. Med. Biol. 19; 699-677. A review of cancer imaging with anti-CEA antibodies is provided by Goldenberg D. M., Int. J. of Biol. Markers 1992, 7; 183-188. Should any method practised on the human or animal body be a method of actual diagnosis of a disease, the present invention of course extends to specific binding members directed against target polypeptides as disclosed, for use in any such method.

ATPase enzymatic activity has been reported for Cdc6 and for MCM proteins. (Zwerschke et al., 1994, *J. Biol. Chem.* 269, 23351-23356; Ishimi et al. Cold Spring Harbor Meeting on Eukaryotic DNA Replication, 3-7 Sep. 1997). These proteins may have other enzymatic activities, for instance helicase activity as reported by Ishimi at al., (Ibid.). The level of a target protein in accordance with the present invention may be assessed by means of determination of its enzymatic activity in a sample. For instance, specific chromogenic substrates have been developed for the enzymatic activity of enzymes such as horseradish peroxidase (diaminobenzidine) and β-galactosidase (X-GAL).

Cdc6, MCM5 or other target protein expression may be assessed at the nucleic acid level, for instance by determining mRNA levels. Williams et al., (Cold Spring Harbor Meeting On Eukaryotic DNA Replication, 3-7 Sep. 1997) have reported expression of Cdc6 mRNA at the base of the intestinal crypts of the mouse gut. Methods for RNA detection are well known in the field, and include Northern blotting, dot blotting, in situ hybridisation, quantitative RT-PCR. Nucleic acid isolated and/or purified from one or more cells or a nucleic acid library derived from nucleic acid isolated and/or purified from cells (e.g. a cDNA library derived from mRNA isolated from the cells), may be probed under conditions for selective hybridisation and/or subjected to a specific nucleic acid amplification reaction such as the polymerase chain reaction (PCR). Binding of a probe to target nucleic acid may be measured using any of a variety of techniques at the disposal of those skilled in the art. For instance, probes may be radioactively, fluorescently or enzymatically labelled. Other methods not employing labelling of probe include examination of restriction fragment length polymorphisms, amplification using PCR, RNase cleavage and allele specific oligonucleotide probing.

For practical purposes, or at least commercial purposes bearing in mind cost and time, assessment of target protein expression at the protein level is generally preferred over assessment at the nucleic acid level.

Aspects of the present invention will now be illustrated with reference to experimental exemplification. Further aspects and embodiments of the present invention will be apparent to those skilled in the art.

EXAMPLE 1

Preparation of Antibodies

Antibodies for Cdc6 were prepared using the following protocol.

Expressed sequence tags encoding fragments of human Cdc6-like protein (GenBank accession numbers: T90351, H59204, N69246, AA045217, AA099980) were identified on the basis of their weak sequence homology to human Orc1 and yeast Cdc6/Cdc18. Corresponding library clones were obtained from IMAGE Consortium (Research Genetics Inc., USA) and sequenced on both strands using ABI PRISM 377 sequencer (Applied Biosystems). A consensus sequence of all five clones contained an open reading frame of 536 amino acids. Alignment with the subsequently published sequence of human Cdc6 (Williams et al., 1997) revealed 99.7% homology at the protein level. Two separate fragments of human Cdc6 corresponding to amino acids 145-360 and 364-547 were cloned as Xbal-BamHI fragments into pET23a expression vector (Novagen) and expressed in *E. coli* CL41 strain. Recombinant protein fragments were purified by Ni+2 agarose affinity chromatography (Qiagen) and used for immunization. Antibodies were raised and affinity purified as previously described (Romanowski et al., Proc. Natl. Acad. Sci. USA, 1996, 93: 10189-10194). Three antibodies recognised a predominant band of 62 kD in HeLa total cell extracts and nuclear extracts.

Antibodies to MCM5 were prepared as follows:

PCR primers were designed on the basis of the published sequence of human MCM5 (Hu et al., 1993, *Nucl. Acid Res.* 21 5289-5293). A fragment of the MCM5 coding sequence corresponding to amino acids 367-582 was amplified from reverse-transcribed HeLa cDNA and cloned as an SphI-BglII fragment into pQE70 expression vector (Qiagen). The protein was expressed in BL21 E. coli cells and purified using $Ni^{2+}$ agarose affinity chromatography (Qiagen). Antibodies were raised as described in Romanowski et al., Proc. Natl. Acad. Sci. USA, 1996, 93: 10189-10194.

EXAMPLE 2

Relationships of Cdc6 and MCM5 to Cell Proliferation

It has previously been shown by Western blot that the immortal human cell line HeLa expresses Cdc6 and MOMS throughout the cell cycle (Williams et al., Proc. Natl. Acad. Sci. USA, 1997, 94: 142-147; Schulte et al., Eur. J. Biochem., 1996, 235, 144-151). Recently the down-regulation of Cdc6 in quiescent Wi38 human fibroblasts was reported by Williams at al, 1997.

The present inventors have also shown by Western blot that Cdc6 expression is down-regulated when mouse 3T3 fibroblasts are made quiescent by contact inhibition.

The NIH 3T3 cell line was arrested by growing to confluence. Cultures were held in quiescence for 7 days. Cells were released from G0 arrest by trypsin detachment and replating. Soluble (supernatant) and nuclear protein (pellet) extracts were prepared at three-hourly intervals and both extracts were immunoblotted with antibodies against human MCM5, Orc2 and Cdc6.

Orc2 (see Gavin at al. for cloning—Science (1995) 270 1667-1671) remains chromatin bound in quiescent cells (G0) and does not increase appreciably as cells enter the cell cycle. In contrast MCM5 could not be detected in the chromatin bound ction (pellet) of quiescent cells even though the soluble fraction contained significant amounts of MCM5. In contrast to MCM5, Cdc6 was completely absent from quiescent cells but the expression of this protein was rapidly induced as cells re-entered the cell cycle. Similar results were also obtained with the human EJ13 cell line (derived from a bladder carcinoma).

These results provide indication that the absence of Cdc6 in quiescent cells is a general phenomenon.

These studies were extended by immunofluorescence and application of anti-Cdc6 and anti-MCM5 antibodies to whole cells.

Expression of Cdc6 and of MCM5 was found to be also down-regulated when newborn human fibroblasts (NHF) are made quiescent by contact inhibition. NHF were grown to confluence and held in quiescence for three days. Cells were released from G0 arrest by trypsin detachment and replating. Whole cells were then harvested at multiple time points after release up until entry into S-phase. Staining with propidium iodide was used to reveal DNA and results were compared with staining of the samples with anti-Cdc6 and anti-MCM5 antibodies.

Quiescent (G0) cells showed no Cdc6 immunoreactivity, and a very weak signal with anti-MCM5 antibody. However, during entry into cell cycle and S-phase, strong nuclear immunoreactivity for Cdc6 and MCM5 was observed.

These studies might suggest that anti-Cdc6 antibodies could provide a marker for proliferating cells similar to PCNA or Ki67. Neither PCNA nor Ki67 has proved satisfactory for cervical cytology.

EXAMPLE 3

Anti-Cdc6 and Anti-MCM5 Binding Molecules Detect Abnormal (e.g. Tumour) Cells Much More Effectively than PCNA or Ki67 Antibodies Results outlined in Example 2 suggest that Cdc6 expression might resemble that of PCNA or Ki67, neither of which has proved satisfactory for cervical cytology. The present inventors compared antibodies to these proteins on sections of normal or diseased uterine cervix.

Immunostaining of cervical SILs for the conventional proliferation markers PCNA and Ki67 shows different pattern of immunoreactivity when compared with staining for Cdc6 or MCM5. In normal cervix, antibodies against all four antigens showed positive immunostaining of epithelial cells confined to the basal and parabasal layers. No immunostaining of metaplastic, stromal or inflammatory cells was observed. In both low and high grade SILs (LSIL and HSIL) antibodies against Cdc6 and Mcm5 showed positive immunostaining of the majority (>95%) of the abnormal cells. In contrast, immunostaining for PCNA and Ki67 was positive in only a minority population (<30%) of abnormal cells in both grades of SILs. Koilocytes, which are characteristic of LSIL and reflect an HPV cytopathic effect, all showed positive immunostaining with Cdc6 and MCM5, whereas only a minority population (20%) showed positive staining for PCNA or Ki67.

The much greater level of staining of abnormal cells provides a distinct advantage for using anti-Cdc6 or anti-MCM5 binding molecules over anti-PCNA and anti-Ki67 molecules in cervical screening wherein tissue samples are most readily taken by way of smears from the surface of the epithelium.

5 µm sections were cut onto glass slides and de-waxed in xylene. Endogenous peroxidase activity was quenched by incubation in 0.6% hydrogen peroxide in 100% methanol for 3-5 minutes at room temperature. The slides were washed in phosphate-buffered saline for 2×5 minutes and then blocked with approximately 100 µl per section of 10% foetal calf serum (FCS) in phosphate buffered saline (PBS). The slides were drained and excess serum wiped away. Primary antibodies were diluted to 1 in 20 in PBS containing 2.5% FCS, and 25-50 µl was added to each section. Incubation was for 45 minutes at room temperature in a humidified chamber. The slides were then washed for 3×5 minutes in PBS, followed by blocking with 20% rabbit serum for anti-Ki67 or anti-PCNA and 20% donkey serum for anti-Cdc6 or anti-MCM5 in PBS for 15 minutes. After draining the blocking antibody and wiping the slides, biotinylated rabbit anti-mouse secondary antibody (for anti-Ki67 or anti-PCNA) or donkey anti-rabbit (for anti-Cdc6 or anti-MCM5) at 1 in 200 in PBS containing 10% normal human serum was added for 30 minutes at room temperature. After 3×5 minute washes in PBS, streptavidin-biotin-horseradish peroxidase complex was added at 1 in 500 in PBS for 30 minutes at room temperature. Following 3×5 minute PBS washes the substrate diaminobenzidine was added at 1% in 100 mM Tris.Cl (pH 7.6) containing 0.005% hydrogen peroxide, and incubated at room temperature for 5 minutes. The reaction was stopped by rinsing in tap water, and slides were lightly stained with Gill's haematoxylin, dehydrated through graded ethanols and washed 2×6 minutes in xylene. Coverslips were applied with DPX mounting medium.

Serial sections of normal cervix were stained for PCNA, Ki67, MCM5 and Cdc6 using respective antibodies. All these antibodies showed similar patterns of immunoreactivity with positive cells confined to the basal and parabasal layers only.

Serial sections of a low grade SIL (CINI) cervix were stained for PCNA, Ki67, MCM5 and Cdc6 respectively using the antibodies. The dysplasia is prominent in the lower third of the squamous epithelium and is associated with HPV related viral changes (koilocytosis), the latter extending to the surface. PCNA and Ki67 show patchy focal immunoreactivity which is confined to the lower ⅓ of the epithelium and in which only a small proportion of the atypical cells are positively stained. In contrast Cdc6 and MCM5 show full thickness immunoreactivity with positive staining of all atypical cells including the koilocytes in the more superficial layers of the epithelium.

Serial sections of a high grade SIL were stained using PCNA, Ki67, MCM5 and Cdc6 antibodies respectively. Dysplasia is present throughout all layers of the epithelium. PCNA and Ki67 show similar patterns of immunoreactivity with full thickness staining but in which only a minority population of the atypical cells are positive (up to approximately 30%). Cdc6 and MCM5 also show full thickness staining of the epithelium. However, in marked contrast to PCNA and Ki67, Cdc6 and MCM5 show positive staining of all atypical cells.

These results are indicative of the particular usefulness of using anti-Cdc6 or anti-MCM5 specific binding molecules in assessing the state of a cervix by means of determining binding to a smear sample. Smears sample only a top surface layer of cells from the cervix, so it is important to have a high level of staining. Such high-level staining obtained with anti-Cdc6 and with anti-MCM5 on the early stage abnormality (low grade SIL, CINI), not shown with anti-PCNA nor anti-Ki67, is very significant. Furthermore, the full thickness staining obtained using anti-Cdc6 and anti-MCM5 antibodies on LSIL samples, but not anti-PCNA nor anti-Ki67 antibodies, highlights the particular usefulness of the former for assessing smear samples for early stage potential pre-malignancy.

EXAMPLE 4

Cdc6 and MCM5 Antibodies Detect Abnormal Cells in Cervical Smears

Example 3 demonstrates the value of anti-Cdc6 and anti-MCM5 binding molecules for detecting potentially pre-malignant lesions in sections of the uterine cervix. Further experimental results show that they are equally effective in detecting abnormal cells in cervical smear preparations.

Cervical smears were fixed for 10 minutes in formaldehyde (4% freshly prepared from paraformaldehyde in phosphate-buffered saline). The fixed material was then stained with anti-Cdc6 antibodies (1:200) or anti-MCM5 antibodies (1:200) followed by donkey anti-rabbit polyclonal antibody conjugated to fluorescein isothiocyanate (Amersham; 1:100). Total. DNA was labelled by propidium iodide. Images were obtained using scanning laser confocal microscopy (Bio-Rad MRC 1024). In these images total DNA is red, Cdc6 or MCM5 immunostaining is green and so immunoreactive nuclei appear yellow.

Examples of normal cervical smears showed a characteristic strip of parallel arranged endocervical cells and a mixed population of superficial and metaplastic squamous cells. There was no evidence of specific anti-Cdc6 or anti-MCM5 immunoreactivity with any of the antibodies tested.

Abnormal smears containing dyskaryotic cells (atypical squamous cells) showed positive staining with three different anti-Cdc6 antibodies and with an anti-MCM5 antibody. Koilocytes also showed strong immunoreactivity with anti-Cdc6 and anti-MCM5 antibodies. None of the adjacent normal superficial squamous/metaplastic cells shows Cdc6 or MCM5 immunoreactivity.

Results were obtained using different anti-Cdc6 antibodies, preferentially staining LSIL cells, including koilocytes, against a very low background in smears of normal cervix, or in normal cells in smears from abnormal cervix. These results were also obtained using an anti-MCM5 antibody.

Similar results were seen with antibodies against MCM5.

EXAMPLE 5

Cdc6 and MCM5 Antibodies Preferentially Stain Cancer Cells in the Breast

Anti-Cdc6 and anti-MCM5 antibodies were tested on another site of common cancers, the breast. Breast tissue fixing and staining was as described in Examples 3 and 4 for cervical smears.

Anti-Cdc6 and anti-MCM5 antibodies were tested on a range of breast cancers.

Whereas the normal breast showed no evidence of immunostaining, strong positive staining was observed with both anti-Cdc6 and anti-MCM5 antibodies in a variety of histological types of breast cancer including low and high grade invasive ductal carcinoma. A low grade mucosal carcinoma also showed strong positive staining with both antibodies. Importantly, normal stromal cells adjacent to cancer were negative.

EXAMPLE 6

Analysis of Blood Samples

Archival blood samples from patients with disseminated metaplastic disease are assayed for the presence of MCM5 and CDC6 using an enzyme-linked immunosorbent assay as described in Williams et al. *Clin. Chem. Acta*, 1986, 155, 329-344. The amount of soluble MCM5 and CDC6 in serum is correlated with tumour load.

EXAMPLE 7

Comparison of Smears and Frozen Sections with Paraffin Wax Embedded Tissue Sections with Antigen Retrieval Immunoperoxidase staining of 5 μm sections of formalin fixed paraffin wax embedded tissue sections of normal cervix (seven samples), LSIL (five samples), HSIL (six samples) and squamous cell carcinoma (six samples) was performed with antibodies against Ki67, PCNA, MOMS and Cdc6.

5 μm sections were cut onto glass slides and de-waxed in xylene. Endogenous peroxidase activity was quenched by incubation in 0.6% hydrogen peroxide in 100% methanol for 30 minutes at room temperature. The slides were washed for 2 minutes in ultrapure water and then pressure cooked for 2 minutes in sodium citrate buffer. The slides were washed in Tris buffered saline (TBS) for 2×5 minutes and then blocked with approximately 100 μl per section of 10% goat serum in TBS. The slides were drained and excess serum wiped away. Primary antibodies were diluted to 1 in 200 in TBS containing 1% BSA, and 100 μl was added to each section. Incubation was overnight at 4° C. in a humidified chamber. The slides were then washed for 3×5 minutes in TBS, followed by biotinylated goat anti-rabbit secondary antibody at 1 in 500 in TBS containing 1% BSA for 30 minutes at room temperature.

After 3×5 minute washes in TBS, streptavidin-biotin-horseradish peroxidase complex was added at 1 in 500 in TBS for 30 minutes at room temperature. Following 3×5 minute TBS washes the substrate diaminobenzidine was added at 1% in TBS containing 0.005% hydrogen peroxide, and incubated at room temperature for 10 minutes. The reaction was stopped by rinsing in tap water, and slides were lightly stained with haematoxylin, dehydrated through graded ethanols and cleared in xylene. Coverslips were applied with DPX mounting medium.

Immunoperoxidase staining of frozen tissue sections of normal cervix (eight samples), HSIL (nine samples) and LSIL (eight samples) was performed with antibodies against PCNA, Ki67, MCM5 and Cdc6.

Frozen sections were fixed for 10 minutes in acetone. Endogenous peroxidase activity was quenched by incubation in 0.6% hydrogen peroxide in 100% methanol for 30 minutes. Sections were then washed in TBS and blocked overnight with 10% goat serum in TBS. Primary antibodies were diluted 1/200 in TBS containing 1% BSA and incubated overnight at 4° C. The secondary antibody procedure was then followed as described above for fixed tissue sections.

The sensitivity of staining with anti-MCM5 and anti-Cdc6 antibodies was much higher than with anti-PCNA and anti-Ki67 antibodies when applied to the frozen sections.

On the normal, LSIL and squamous cell carcinoma tissue fixed in formalin, paraffin embedded and exposed to pressure cooking, anti-PCNA, anti-MCM7, anti-MCM5 and anti-Cdc6 gave similar patterns of staining. Ki67 in comparison was much less sensitive with only focal weak staining of LSIL and squamous cell carcinoma.

EXAMPLE 8

Staining with Anti-MCM7 Antibodies on Frozen Sections and on Tissues Subject to Antigen Retrieval Four frozen sections of cervix classified as HSIL were stained with anti-MCM7 antibody.

Staining was observed with the same pattern as for staining with anti-Cdc6 and anti-MCM5 antibodies.

This result differs from that of Hiraiwa et al. (*Int. J. Cancer*, 1997, 74: 180-184) who found similar immuno-staining patterns for PCNA and MCM7 (hCDC47) in several human tissues and three types of human tumour which had been subjected to antigen retrieval protocols.

However, consistent with Hiraiwa et al., staining patterns obtained for anti-MCM7 antibodies on normal cervix, LSIL and squamous cell carcinoma paraffin wax embedded tissue sections subject to antigen retrieval were found to be similar to those obtained for anti-PCNA antibodies. As indicated in Example 7, staining patterns for anti-MCM5 and anti-Cdc6 antibodies on such sections so prepared were also similar to those for anti-PCNA antibodies.

EXAMPLE 9

Staining with Anti-MCM2 Antibodies

Rabbit polyclonal anti-human MCM2 was used to stain two frozen sections of normal cervix and four frozen sections of HSIL (each of which included normal cervical epithelium).

Normal ectocervix showed staining of nuclei in the basal layer only, with no expression in superficial differentiated cells. In contrast, there was nuclear staining of HSIL cells throughout the full thickness of the abnormal epithelium. Endocervical cells were negative.

EXAMPLE 10

Staining with Anti-MCM3 Antibodies

Rabbit polyclonal anti-human MCM3 was used to stain a frozen section of normal cervix and two frozen sections of HSIL, (each of which included normal cervical epithelium).

Normal ectocervix showed rather granular staining of nuclei in the basal layer only, with no nuclear expression in superficial differentiated cells. Some background staining of keratinocyte cytoplasm was seen. In contrast, there was nuclear staining of HSIL cells throughout the full thickness of the abnormal epithelium. There was some staining of endocervical mucus, although the nuclei of endocervical cells were negative.

Polyclonal anti-human MCM3 was also used to stain four smears of HSIL and two smears of LSIL each of which included normal cervical cells). There was nuclear staining of SIL cells in each case. In addition, there was background cytoplasmic staining of keratinocytes and some staining of endocervical cell nuclei at the dilution of primary antibody used.

Polyclonal anti-*Xenopus* MCM3 was used to stain a frozen section of HSIL. Crass-reactivity of the anti-*Xenopus* MCM3 antibodies with human MCM3 was confirmed by Western blotting and localisation on tissue sections. There was nuclear staining of HSIL cells throughout the full thickness of the abnormal epithelium.

EXAMPLE 11

Staining with Anti-MCM4 Antibodies

Rabbit polyclonal anti-human MCM4 was used to stain a frozen section of normal cervix and two frozen sections of HSIL (each of which included normal cervical epithelium).

Normal ectocervix showed rather granular staining of nuclei in the basal layer only, with no nuclear expression in superficial differentiated cells. Some background staining of keratinocyte cytoplasm was seen. In contrast, there was nuclear staining of HSIL cells throughout the full thickness of the abnormal epithelium, with strong staining of surface nuclei. There was weak staining of endocervical cell nuclei at the dilution of primary antibody used.

Polyclonal anti-human MCM4 was also used to stain two smears of HSIL (each of which included normal cervical cells). There was nuclear staining of HSIL cells in each case. In addition, there was background cytoplasmic staining of keratinocytes and some staining of endocervical cell nuclei at the dilution of primary antibody used.

EXAMPLE 12

Staining with Anti-MCM6 Antibodies

Rabbit polyclonal anti-human MCM6 was used to stain a frozen section of normal cervix and two frozen sections of HSIL (each of which included normal cervical epithelium).

Normal ectocervix showed strong staining of nuclei in the basal layer only, with no nuclear expression in superficial differentiated cells. In contrast, there was strong nuclear staining of HSIL cells throughout the full thickness of the abnormal epithelium. There was some staining of endocervical mucus, but minimal staining of endocervical cell nuclei.

Polyclonal anti-human MCM6 was also used to stain four smears of HSIL and four smears of LSIL (each of which included normal cervical cells). There was nuclear staining of SIL cells in each case. In addition, there was background cytoplasmic staining of keratinocytes and some staining of endocervical nuclei at the dilution of primary antibody used

EXAMPLE 13

Further Staining Experiments with Anti-MCM7 Antibodies

Rabbit polyclonal anti-human MCM7 was used to stain three frozen sections of normal cervix, six frozen sections of HSIL and a frozen section of a cervical SCC (each of which included normal cervical epithelium).

Normal ectocervix showed staining of nuclei in the basal layer only, with no nuclear expression in superficial differentiated cells. Some background staining of keratinoctye ectoplasm was seen. In contrast, there was strong nuclear staining of the large majority of HSIL cells throughout the full thickness of the abnormal epithelium. There was some staining of endocervical mucus, and weak staining of endocervical cell nuclei at the dilution of primary antibody used.

Polyclonal anti-human MCM7 was also used to stain two smears of HSIL and two smears of LSIL (each of which included normal cervical cells). There was nuclear staining of SIL cells in each case. In addition, there was background cytoplasmic staining of keratinocytes and some staining of endocervical cell nuclei at the dilution of primary antibody used Polyclonal anti-*Xenopus* MCM7 (confirmed to cross-react with human MCM7 by Western blotting and localisation on tissue sections) was used to stain a frozen section of HSIL. There was nuclear staining of HSIL cells throughout the full thickness of the abnormal epithelium.

Methods
Preparation of Cervical Smears

Fresh smears were fixed (5 minutes in 50:50 acetone: methanol) and air dried. After quenching endogenous peroxidase activity (as above), cells were permeabilised (4 mM sodium deoxycholate for 10 minutes), washed (TBS with 0.25% Triton X-100) and blocked overnight with 10% goat serum in TBS. Primary antibodies were diluted 1/200 in TBS containing 1% BSA and incubated overnight at 4° C. The slides were then washed 3×5 minutes in TBS, followed by biotinylated rabbit secondary antibody (Dako) at 1 in 500 in TBS containing 1% BSA for 30 minutes at room temperature. After 3×5 minute washes in TBS, streptavidin horseradish peroxidase complex (Dako) was added at 1 in 500 in TBS for 30 minutes at room temperature. Following 3×5 minute TBS washes the substrate diaminobenzidine was added at 1% in TBS containing 0.005% hydrogen peroxide, and incubated at room temperature for 10 minutes. The reaction was stopped by rinsing in tap water, and slides were lightly counter-stained with haematoxylin, dehydrated through graded ethanols and cleared in xylene. Coverslips were applied with DPX mounting medium.

Immunofluorescence

Freshly collected cervical smear material was suspended in 0.5 ml PBS and fixed by addition of 0.5 ml 8% formaldehyde and spun onto polylysine coverslips. Coverslips were processed as described in Romanowski et al., Proc. Natl. Acad. Sci. USA, 1996, 93: 10189-10194. Following blocking in 5% BSA/PBS/TritonX-100 and SDS they were incubated with primary antibody, washed, incubated with secondary antibody (FITC conjugated anti-rabbit antibody Amersham 1:100) and counterstained for DNA with propidium iodide/ RNAse A (both Sigma at 50 ng/ml), washed and mounted in glycerol/PBS/phenylenediamine.

Fluorescent images were collected on a BioRad MRC 1024 scanning laser confocal microscope using a two channel (FITC & Texas Red) method. For some images confocal series at 1-2 µm steps were collected and then projected as a single frame. Normal and tumour breast tissue was collected freshly from mastectomy specimens. Thin slices (<1 mm) were fixed in 4% paraformaldehyde for 30 minutes and then processed as above but allowing longer times for both antibody incubations and washings.

EXAMPLE 14

A Blinded Comparison of an Embodiment of the Present Invention with Standard Pap Staining A blinded trial was performed to compare detection efficiency using antibodies against MCM5 with standard Pap staining performed on smears obtained from females attending colposcopy outpatient clinics at local hospitals.

Table 1 shows that of 26 cases assessed as positive by routine Pap stain, all 26 were also scored positive by the antibody test in accordance with the present invention. Of cases scored negative by routine Pap stain, 13 were also scored negative by the antibody test.

Of the remaining three, one contained stained immature metaplastic squamous cells showing reactive changes in an inflammatory background. The other two were confirmed as containing abnormal (LSIL) cells on re-examination of the Pap stain, i.e. were false-negatives of the kind which the present invention may be used to eliminate.

These results demonstrate no loss of information from the Pap stain, only a gain of information using an antibody test in accordance with the present invention. This allows for any possible failure of the antibody test to be underwritten using the conventional Pap stain.

EXAMPLE 15

Analysis of Urine Samples of Patients with Urinary Tract Malignancies

A Dissociation Enhancement Lanthanide Fluorescence Immunoassay ("DELFIA") was established for detection of human MCM5 using two different rabbit polyclonal anti-hMCM5 antisera.

The basis of the sandwich assay is the immobilisation of an excess of specific antibody to a surface (here polystyrene microtiter wells)—i.e. the "capture" antibody. Following the primary antibody-binding reaction a second (here europium) labelled antibody with a different epitope specificity is added in excess. After the immunoreaction has been completed the excess materials are washed away and, following the addition of enhancement solution, (Wallac Oy) time resolved fluorescence is measured in a time resolved fluorometer. The signal is proportional to the concentration of the analyte.

The following assay has been employed:
1. Coating with polyclonal rabbit anti MCM5 Ab (1600 ng/well) overnight (4° C.);
2. 3× Washing with DELFIA wash buffer (Wallac Oy);
3. Blocking in 5% BSA/PBS for 1 hr;
4. 3× Washing with DELFIA wash buffer (Wallac Oy);
5. Primary antibody-binding reaction (1:3 dilution of analyte in Wallac multi buffer with 0.02% TWEEN) overnight (4° C.)

6. 4× Washing with DELFIA wash buffer (Wallac Oy);

7. Secondary antibody-binding reaction with europium labelled polyclonal rabbit anti-MCM5 Ab (4 $^{20}$Eu/IgG) for 3 hrs;

8. 6× Washing with DELFIA wash buffer (Wallac Oy);

9. Addition of enhancement solution 10 min incubation with shaking. Measurement of time resolved fluorescence in a time resolved fluorometer (Wallac Oy).

Using polyclonal rabbit anti-MCM5 antisera from two different rabbits and recombinant human MCM5 in 5% BSA/PBS as the analyte a standard curve between 13 pM and 41250 pM was achieved. The concentration of hMCM5 in a specimen was determined by comparison of the DELFIA assay counts of the sample to a standard curve made from recombinant hMCM5 5% BSA/PBS. Even better sensitivity is to be expected for when monoclonal antibodies are used.

Urine specimens from patients with urinary tract malignancies at Addenbrookes Hospital, Cambridge, UK, were centrifuged (50-150 ml) at 3000 rpm (SIGMA 4K10, 7 min, 4° C.) and soluble fractions from the cell pellet were produced by hypotonically swelling, douncing and salt extraction of DNA-bound proteins. Soluble fractions were assayed using the MCM5 DELFIA and the biochemical data compared with diagnostic reports for urology pathology services at the hospital.

Of 5 samples determined clinically to be positive for malignancy, 4 scored positive using the DELFIA in accordance with the invention (80%) showing measurable amounts of MCM5 (29-85 pM). Of 6 samples determined clinically to be negative for malignancy, all gave responses similar to the zero standard with the DELFIA.

EXAMPLE 16

Analysis of Blood Samples of Patients with Acute and Chronic Leukaemia/Lymphoma

The DELFIA described in Example 15 was used in testing blood samples obtained from patients with acute and chronic leukaemia/lymphoma at Addenbrookes Hospital, Cambridge. Blood was centrifuged at 3000 rpm (SIGMA 4K10, 7 min, 4° C.) and soluble fractions from the cell pellet were produced by hypotonically swelling, douncing and salt extraction of DNA bound proteins. Soluble fractions were subsequently assayed using the DELFIA.

Of 6 malignant cases, 5 tested positive using the DELFIA in accordance with the present invention (83%) showing measurable amounts of MCM5 (24-1945 pM). Of 6 control samples (Blood from diabetic outpatients) all gave responses similar to the zero standard.

EXAMPLE 17

Serological Detection of Metastatic Malignancy

Assays were performed with serum from patients with metastatic breast and ovarian cancer at Addenbrookes Hospital, Cambridge, UK using the DELFIA described in Example 15.

Two Sarcoma cases and three carcinoma cases (breast and ovary adenocarcinoma) showed measurable amounts of MCM5.

EXAMPLE 18

Preparation of "Pan-MCM" Polyclonal Antibody for Use in the Invention

A polyclonal antibody preparation able to bind MCM2, MCM3, MCM4, MCM5, MCM6 and MCM7 was obtained as follows.

The peptide VVCIDEFDKMSDMRTAC (SEQ ID NO:1), corresponding to a consensus sequence common to the MCM family of proteins, was synthesized using t-BOC chemistry. The peptide was conjugated to PPD (purified protein derivative—tuberculin).

Rabbits were immunized by injection at 21 day intervals. 10 days after the third immunization serum was harvested and was used in subsequent experiments (referred to as "pan-MCM" antibody in the following experimental examples).

EXAMPLE 19

Staining of Normal Breast and Breast Carcinoma Tissues with Anti-CDC6, Anti-MCM2, Anti-MCM5, Anti-MCM7 and Pan-MCM Antibodies Histological specimens of normal breast (recipients of breast reduction operations) and biopsy-proven ductal and lobular carcinomas were stained with antibodies against CDC6, MCM2, MCM5 and MCM7 and a pan-MCM antibody. The anti-MCM2 antibody was the BM28 mouse monoclonal antibody available commercially from Transduction Laboratories (see their 1998 Antibody Catalog). Staining was performed individually for each antibody as described.

Both formalin-fixed, paraffin embedded specimens which were the subject of pressure cooking, and frozen specimens were examined.

Formalin fixed, paraffin embedded human tissues obtained for diagnostic biopsy or after resection at Addenbrooke's Hospital were utilised in accordance with ethical guidelines approved by the hospital. Five micron sections were cut from these tissues onto APES (aminopropyltriethoxysilane) coated slides, dewaxed in xylene and taken through alcohols to water. The tissue was pressure cooked in citrate buffer to facilitate epitope retrieval, following by washing in Tris-buffered saline (TBS). Endogenous peroxidase activity was quenched by incubation in 0.6% hydrogen peroxide in TBS for 30 minutes.

Sections were washed in TBS and blocked with 10% goat serum in TBS for up to 2 hours. Primary antibodies were diluted in TBS containing 0.1% Triton and 1% Bovine serum albumen (BSA). One hundred microlitres was added to each section and the slides were incubated at 4° C. in a humidified chamber.

The slides were then washed in TBS containing 0.025% Triton, followed by incubation in biotinylated goat anti-rabbit secondary antibody (DAKO) at 1:500 in TBS containing 1% BSA for 1 hour at room temperature. After washes in TBS, a strepavidin horseradish peroxidase system using the substrate diaminobenzidine was used to stain the slides. The reaction was stopped by rinsing in water and lightly counter-stained with Harris' haematoxylin, dehydrated through graded ethanols and cleared in xylene. Coverslips were applied with DEPEX mounting medium.

Frozen sections were prepared as described above in Example 7 except blocking with 10% goat serum was for 30 minutes and not overnight.

In the normal breast tissue, only 1-3% of ductal and lobular cells stained positive. Stromal cells were negative.

50-80% of abnormal cells in a variety of breast carcinomas, including low and high grade lesions and lobular and ductal type, showed positive staining, with surrounding stromal cells and inflammatory cells remaining unstained.

These results were obtained individually with each of the antibodies.

A comparison was made with anti-PCNA and anti-Ki67 antibodies. On the paraffin sections, anti-PCNA staining gave similar results to anti-MCM5 and anti-CDC6 while anti-Ki67 antibodies gave only weak, focal staining. On the frozen sections, staining with anti-MCM and anti-CDC6 antibodies gave much better results than either anti-PCNA or anti-Ki67 antibodies.

EXAMPLE 20

Staining of Normal Prostate and Adenocarcinoma of the prostate using antibodies against MCM5, MCM7 and Pan-MCM Paraffin-embedded histological specimens of normal tissue and adenocarcinoma of the prostate, prepared as described for breast tissue in Example 19, were stained with anti-MCM5, anti-MCM7 and pan-MCM antibodies in separate experiments.

Normal cases showed positive staining of less than 10% of cells with each antibody, whereas adenocarcinomas showed staining of 30-50% of tumour cells, with surrounding stromal cells and inflammatory cells remaining unstained.

EXAMPLE 21

Staining of Normal Colon and Carcinoma of the Colon Using Antibodies Against MCM2, MCM5, MCM7, Pan-MCM and CDC6

Histological resection specimens of colon adenocarcinoma and tubulovillous adenoma were stained separately with antibodies against MCM2, MCM5, MCM7, pan-MCM and CDC6. Normal specimens were also stained with these antibodies.

In normal tissue, the staining for each antibody was only seen in the lower third of colonic crypts, with more superficial differentiated cells in the crypts remaining unstained.

In both tubulovillous adenoma and adenocarcinoma tissues, more than 50% of tumour cells were positive for staining with each antibody, with no staining of surrounding connective tissue elements.

Both frozen and paraffin-embedded samples were examined, as for breast tissue in Example 19. The results were similar as between anti-MCM and anti-CDC6 antibodies on the one hand and anti-PCNA and anti-Ki67 antibodies on the other, i.e. on frozen samples the staining with anti-MCM and anti-CDC6 antibodies was superior to that obtained using anti-PCNA and anti-Ki67 antibodies.

EXAMPLE 22

Staining of Normal Tissue and Carcinoma of the Lung, with Antibodies Against MCM2, MCM5, MCM7 and Pan-MCM Paraffin embedded histology specimens of biopsies or resections from patients with squamous cell carcinoma or adenocarcinoma of the lung were stained separately with anti-MCM2, anti-MCM5, anti-MCM7 and pan-MCM antibodies. The specimens were prepared as described for breast tissue in Example 19. Staining was compared with staining on normal parenchymal lung tissue.

In the normal tissue, the stained proliferative fraction was very low.

In all carcinomas, more than 30% of tumour cells were positive, with no staining of surrounding inflammatory or connective tissue cells.

EXAMPLE 23

Staining of Bladder, Both Normal and Carcinoma, with Anti-MCM2, Anti-MCM5, Anti-MCM7, Pan-MCM and Anti-CDC6 Antibodies Histological specimens from biopsies of transitional cell carcinomas taken at cystoscopy were stained with anti-MCM2, anti-MCM5, anti-MCM7, pan-MCM and anti-CDC6 antibodies.

In normal bladder tissue, there was strong staining of the basal layer of transitional epithelium with the more superficial differentiated cells remaining unstained.

In fragments containing carcinoma in situ, the full thickness of dysplastic cells stained positive.

Cases of invasive transitional cell carcinoma showed 50-100% nuclear staining of tumour cells, with negative stromal and inflammatory components.

Both frozen and paraffin-embedded samples were examined, as for breast tissue in Example 19. The results were similar as between anti-MCM and ant CDC6 antibodies on the one hand and anti-PCNA and anti-Ki67 antibodies on the other, i.e. on frozen samples the staining with anti-MCM and anti-CDC6 antibodies was superior to that obtained using anti-PCNA and anti-Ki67 antibodies.

EXAMPLE 24

Staining of Various Skin Samples with Anti-MCM5 Antibodies

Histological samples from normal skin, hyperplastic conditions (including psoriasis), solar keratoses, Bowen's disease and invasive squamous cell carcinomas were stained with anti-MCM5 antibodies.

Normal skin showed staining of predominantly the basal layer of the epithelium with occasional cells in the lower third of the epidermis also staining, but more superficial differentiated cells remaining unstained.

In cases of psoriasis, there was more predominant staining in the lowermost 3-4 layers on the epidermis, reflecting the increased turnover rate of the skin.

Solar keratoses and Bowen's disease (carcinoma in situ) showed staining of all dysplastic cells in the epidermis, up to full thickness.

Invasive squamous cell carcinomas showed staining of greater than 70% of cells, with well differentiated tumours showing small foci of negative differentiated cells adjacent to keratin pearls.

EXAMPLE 25

Staining of Larynx with Anti-MCM5 Antibodies

Histological samples of normal and carcinoma larynx, prepared as for the paraffin embedded specimens of breast tissue described in Example 19, were stained with anti-MCM5 antibody.

Normal cases showed staining of basal proliferating epithelial cells only (less than 10%).

Carcinomas showed greater than 50% cells with nuclear staining. Stromal and inflammatory cells were negative throughout.

EXAMPLE 26

Staining of Oesophagus with Anti-MCM5 Antibodies

Histological samples of normal and carcinoma oesophagus, prepared as for the paraffin embedded specimens of breast tissue described in Example 19, were stained with anti-MOMS antibody.

Normal cases showed staining of basal proliferating epithelial cells only (less than 10%).

Carcinomas showed greater than 50% cells with nuclear staining. Stromal and inflammatory cells were negative throughout.

EXAMPLE 27

Staining of Bronchus with Anti-MCM5 Antibodies

Histological samples of normal and carcinoma bronchus, prepared as for the paraffin embedded specimens of breast tissue described in Example 19, were stained with anti-MCM5 antibody.

Normal cases showed staining of basal proliferating epithelial cells only (less than 10%).

Carcinomas showed greater than 50% cells with nuclear staining. Stromal and inflammatory cells were negative throughout.

EXAMPLE 28

Staining of Lymph Nodes, Both Normal and with a Range of Lymphomas, Using Anti-MCM5 Antibody Both frozen and paraffin embedded histological samples were prepared of reactive lymph nodes and a range of Hodgkin's and non-Hodgkin's lymphomas as is described for breast tissue in Example 19.

Reactive lymph nodes showed strong staining of cells in the germinal centre of lymphoid follicles and occasional scattered positive cells in the parafollicular areas.

Lymphomas showed greater than 50% nuclear staining of malignant lymphoid cells.

EXAMPLE 29

Analysis of Urine Cytology Smears with Anti-MCM5 Antibody

Urine samples were collected from patients with known transitional cell carcinoma and from normal patients attending urology clinic. Twenty millilitres of urine was spun down at 3,000 g for 10 minutes, supernatant removed and the pellet resuspended in 50 microlitres of supernatant. This was smeared onto an APES slide and fixed in alcohol.

The slides were washed in Tris buffered saline (TBS), then permeabilized in 4 mM sodium deoxycholate for 10 minutes. They were washed with TBS plus 0.025% Triton and blocked with 10% goat serum in TBS for 2 hours. Preabsorbed anti-MOMS antibody was diluted in TBS containing 0.1% Triton and 1% BSA and 200 microlitres was added to each slide. Incubation was overnight at 4° C. in a humidified chamber on an orbital shaker.

The slides were washed in TBS containing 0.025% Triton, followed by incubation in biotinylated goat anti-rabbit secondary antibody (DAKO) at 1:500 in TBS containing 1% BSA for 1 hour at room temperature. Endogenous peroxidase was blocked with 0.6% hydrogen peroxide in TBS for 10 minutes, followed by wash in TBS. A streptavidin horseradish peroxidase system using the substrate diaminobenzidine was used to stain the slides. The reaction was stopped by rinsing in water and the slides were lightly stained with Harris' haematoxylin followed by staining with Orange G and EA50 (PAP stain).

In six cases of transitional cell carcinoma, urine cytology smears prepared in this way and stained with anti-MCM5 antibodies showed strong staining of all malignant transitional cells, with unstained inflammatory and squamous cells in the background. Similar smears produced from urine of normal people attending urology clinics showed no staining of squamous or normal transitional cells.

EXAMPLE 30

DELFIA of Normal Cervical Samples and Cervical Samples from Patients with Squamous Intraepithelial Lesions A dissociation enhancement lanthanide fluorescence immunoassay (DELFIA) was established for detection of human MCM5 using two different rabbit polyclonal anti-MCM5 antisera as described in Example 15 above.

Two samples of normal cervix and two samples of HSIL cervix were analysed. The tissue samples were solubilised by hypotonically swelling and douncing followed by salt extraction of DNA bound particles.

The two normal samples gave responses similar to the zero standards.

The two HSIL samples scored positive, indicating that abnormality in a cervical sample can be detected using immunoassay.

EXAMPLE 31

Staining of Various Carcinoma Tissues with Anti-MCM5 Antibody

Histological specimens of various carcinomas and leukaemic bone marrow were stained with anti-MCM5 antibodies, the results being as follows:

Stomach carcinoma showed greater than 50% staining of tumour cells.

Kidney carcinoma showed 30-50% staining of tumour cells.

Ovary carcinoma showed 30-50% staining of tumour cells.

Testis carcinoma showed 30-50% staining of tumour cells.

Bone marrow of acute leukaemia showed greater than 90% staining of tumour cells.

EXAMPLE 32

Staining of Colon Smears

Fecal material was collected from healthy patients and surface exfoliated colonocytes were extracted from the fecal samples by means of magnetic beads coated with epitheliaspecific antibodies, supplied by Dynal AS (Oslo, Norway), using the process as described in WO97/09600.

The extracted mixture of magnetic beads and epithelial cells was washed in TBS (Tris-buffered saline) containing 0.025% Triton. After fixation in 4% buffered paraformaldehyde, the cells were washed in TBS and smears were made from the resulting cell pellet. These were then treated as for smears from the urine samples.

The PAP stained smears showed a mixture of magnetic beads, some cellulose and cell debris; many columnar epithelial cells from the colon and a few squamous cells from the anal canal were present.

On staining with anti-MOMS antibodies, similar results are obtained for normal and abnormal cells as for the bladder or cervix.

EXAMPLE 33

Staining of Bowel Sections of Patients with Ulcerative Colitis

Paraffin-embedded sections of bowel from cases of active ulcerative colitis were stained with antibodies against MCM5.

In all sections tested approximately 50% of the surface epithelial cells showed nuclear expression of MCM5 in the inflamed areas. Large numbers of lymphocytes are present in active ulcerative colitis, and these cells also showed frequent nuclear expression of MCM5.

Sections of quiescent ulcerative colitis (i.e. with no active inflammation) were also analysed. In all of these the surface epithelial cells showed no staining for MCM5. Of the small numbers of lymphocytes present in quiescent ulcerative colitis, only a rare cell showed nuclear staining for MCM5.

In the paraffin-embedded sections, staining of active and quiescent ulcerative colitis was found to be similar for MCM5 and PCNA.

EXAMPLE 34

Staining of Bowel Sections of Patients with Crohn's Disease

Staining of paraffin-embedded section of active Crohn's disease bowel showed nuclear expression of MCM5 in surface epithelial cells adjacent to regions of ulceration and inflammation. Lymphocytes in the inflamed tissue also showed frequent nuclear expression of MCM5.

Quiescent Crohn's disease bowel tissue was also tested and both the surface epithelial cells and the small numbers of lymphocytes present were negative for MCM5.

Similar findings were obtained for anti-MCM5 antibodies as for anti-PCNA antibodies on the paraffin-embedded cases of active and quiescent Crohn's disease.

A comparison between anti-MCM5 and anti-PCNA staining made on frozen sections and paraffin-embedded sections shows that in frozen sections staining with anti-MCM5 antibodies is superior to staining with anti-PCNA antibodies, with more nuclei being stained.

EXAMPLE 35

Staining of Normal and Cancerous Endometrium with Anti-MCM5 Antibodies

Frozen and paraffin-embedded sections of normal and cancerous endometrium were stained with anti-MCM5 antibodies.

Good staining was shown in the cancerous endometrium as compared with the normal tissue, and superior in the frozen sections compared with the paraffin-embedded.

EXAMPLE 36

Staining of Cervical Smear Cell Monolayer (Thin Prep)

After making a smear on an APES slide, the brush/spatula used for taking the cervical smear was placed in 75% methanol and the remaining cells removed by vortexing. The suspension of cells was layered on to 20% sucrose, spun at 1,000 rpm for 2 minutes in a MSE Harrier centrifuge and the top layer removed and discarded. The remaining layer was spun at 3,000 rpm for 5 minutes and the cell pellet resuspended in 200 microlitres of water. Fifty microlitres was placed on each slide, the cells allowed to settle and the water removed. The slides were then carried through as in Example 29 (urine cytology smears) and PAP stained.

In various experiments, results obtained with monolayer smears were the same as those obtained with conventional smears. Use of monolayer preparations may be advantageous in that mucus and the majority of inflammatory cells are removed.

Discussion

The results described herein show that Cdc6 and MCM5 are both down-regulated in normal differentiated tissues in vivo and absent from chromatin in a range of quiescent mammalian cells in culture. This provides some suggestion that these proteins may be of potential value as cell proliferation markers. Hiraiwa et al. demonstrated that MCM7 can be immunolocalised in a variety of tumour types such as benign skin tumours and malignant tumours of the stomach, pancreas and colon, with a similar distribution to PCNA. They concluded that MCM7 immunolocalization could be applied as an index of cell proliferation in tissue sections. However, as noted already above, experts in the field of pathology are sceptical that the measurement of cell proliferation rates in tumours by markers such as PCNA & Ki67 will be of any clinical use, as there is little direct evidence that such markers are a real improvement on conventional histological assessments such as grading and staging, when optimally applied.

The observations reported here show that specific binding molecules directed against Cdc6, MCM5 and MCM7 exhibit a much higher degree of specificity for potential pre-malignant cells in fresh and frozen cervical SILs, than do conventional proliferation markers such as PCNA and Ki67. Anti-Cdc6 and anti-MCM5 are able clearly to discriminate the abnormal cells in LSIL and HSIL from adjacent normal cells, including endocervical, ectocervical, metaplastic and stromal cells.

In view of this, as described anti-Cdc6 and anti-MCM antibodies were applied to cervical smears taken from patients with SILs, and from disease free patients. The results were surprising in the striking degree of specificity and sensitivity observed for these proteins. Strong nuclear and cytoplasmic staining were observed in both neoplastic cells and HPV-infected koilocytes. Positive immunostaining was also identified in metaplastic squamous cells showing borderline abnormalities (atypical squamous cells of uncertain significance). However, the remaining mixed population of normal cells in the smear including ectocervical cells, endocervical cells, squamous metaplastic cells and inflammatory cells (both lymphocytes and neutrophils) were negative for Cdc6 and MCM immunostaining.

The sensitivities of anti-MCM5, anti-Cdc6 and anti-MCM7 are much higher than anti-PCNA when applied to cervical smears and frozen sections, but similar patterns of staining are given by such antibodies when applied to tissue fixed in formalin, paraffin embedded and exposed to antigen retrieval by pressure cooking. Cervical smears and other cytological samples as well as frozen sections are less robust than formalin fixed, paraffin embedded tissue sections and so cannot be subjected to pressure cooking.

The surprising specificity and sensitivity of the Cdc6 and MCM antibodies when applied to cervical smears provides for introduction of a biochemical/immunocytological approach to mass automated cervical screening. Furthermore, these antibodies may help to improve the detection and classification of LSILs, for which there is at present marked intraobserver and interobserver variation in grading, even amongst experts in the field of cervical cytology. The use of these antibodies will also help identify HSILs with greater accuracy and objectivity, thus helping to reduce the high number of false negative results, a major problem associated with the present global cervical screening programmes.

As noted, the further experimental exemplification of assessment of breast tissue, stomach, kidney, ovary, testis and colon, urine samples and blood samples (both of leukaemia/lymphoma patients and of metastatic sarcoma and carcinoma patients), also tissues of inflammatory bowel disease including ulcerative colitis and Crohn's disease, and fecal smears indicates the generality of the aspects of the present invention beyond cervical screening, though assessment of cervical samples, especially cervical smears, is preferred in various embodiments. The application of biochemical techniques is also demonstrated in addition to cytology.

The results of the blinded trial comparing an embodiment of the present invention with assessment of cervical smears using standard PAP smearing, described in Example 14 above, confirm the exciting utility of the invention.

All documents mentioned herein are incorporated by reference.

TABLE 1

Comparison of anti-Mcm5 antibody test versus conventional Pap test in a blind trial of patients recalled to colposcopy clinics

| | | Standard Pap test result | | |
|---|---|---|---|---|
| | | Normal | Low grade | High Grade |
| Anti-Mcm5 antibody test | Presence of positive cells | 3[a] | 9 | 17 |
| | Absence of positive cells | 13 | 0 | 0 |

[a]see text

We claim:

1. A method of determining the presence or absence of dysplastic or neoplastic cervical cells in a test sample containing cells from an individual, wherein the test sample comprises a cervical cytology sample, the method comprising:

contacting the test sample with an antibody or antibody fragment directed against Minichromosome Maintenance protein 6 (MCM6 protein); and determining the amount of binding of said antibody or antibody fragment to said test sample;

whereby an increase in said amount if detected for the test sample compared with a normal sample is indicative of presence of dysplastic or neoplastic cervical cells in said test sample.

2. A method according to claim 1 wherein a population of individuals is screened.

3. A method according to claim 1 wherein the sample is a cervical smear.

4. A method according to claim 3 wherein a population of individuals is screened.

* * * * *